United States Patent
Hazard et al.

(10) Patent No.: US 10,300,275 B2
(45) Date of Patent: May 28, 2019

(54) MAGNET INSTALLATION SYSTEMS AND METHODS FOR USE WITH COCHLEAR IMPLANTS

(71) Applicant: Advanced Bionics AG, Staefa (CH)

(72) Inventors: Steve Hazard, Castaic, CA (US); Sarah Elizabeth Clabeaux, Ventura, CA (US); Charles C. Finley, Stevenson Ranch, CA (US); Lee F. Hartley, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 16/158,591

(22) Filed: Oct. 12, 2018

(65) Prior Publication Data

US 2019/0038900 A1    Feb. 7, 2019

Related U.S. Application Data

(62) Division of application No. 14/764,792, filed as application No. PCT/US2014/019970 on Mar. 3, 2014, now Pat. No. 10,124,167.

(60) Provisional application No. 61/780,977, filed on Mar. 13, 2013.

(51) Int. Cl.
*A61N 1/36* (2006.01)
*A61N 1/375* (2006.01)

(52) U.S. Cl.
CPC ......... *A61N 1/36036* (2017.08); *A61N 1/375* (2013.01)

(58) Field of Classification Search
CPC .. A61N 1/36032; A61N 1/375; A61N 1/0541; A61N 1/36036
See application file for complete search history.

(56) References Cited

U.S. PATENT DOCUMENTS

| | | |
|---|---|---|
| 3,736,933 A | 6/1973 | Szabo |
| 4,317,284 A | 3/1982 | Prindle |
| 4,437,362 A * | 3/1984 | Hurst ................. B25B 9/02 294/65.5 |
| 5,690,226 A | 11/1997 | N'Guyen |
| 6,321,125 B1 | 11/2001 | Kuzma |
| 8,043,303 B2 | 10/2011 | Razvi |
| 1,053,387 A1 | 2/2013 | Hawley |
| 9,308,608 B2 | 4/2016 | Townsend |
| 9,763,686 B2 | 9/2017 | Harnisch |
| 2004/0243177 A1 | 12/2004 | Svehla et al. |
| 2005/0004629 A1* | 1/2005 | Gibson ............. A61N 1/375 607/60 |
| 2005/0070919 A1 | 3/2005 | Lieberman |
| 2005/0082307 A1 | 4/2005 | Tucker |
| 2006/0085042 A1 | 4/2006 | Hastings |
| 2009/0099403 A1* | 4/2009 | Zimmerling ........ A61N 1/372 600/12 |

(Continued)

FOREIGN PATENT DOCUMENTS

WO    WO 2008/109800 A1    9/2008
WO    WO 2009/048999 A1    4/2009

OTHER PUBLICATIONS

PCT International Search and Written Opinion dated Aug. 29, 2014 for PCT App. App. Ser. No. PCT/US2014/019970.

(Continued)

*Primary Examiner* — William J Levicky
(74) *Attorney, Agent, or Firm* — Henricks Slavin LLP

(57) ABSTRACT

Apparatus and methods for installing a magnet into a cochlear implant.

16 Claims, 10 Drawing Sheets

(56) References Cited

U.S. PATENT DOCUMENTS

2010/0125311 A1  5/2010  Choi
2015/0359553 A1  12/2015  Harnisch

OTHER PUBLICATIONS

Communication pursuant to Article 94(3) EPC dated May 29, 2017 for EPO Appl. Ser. No. 14 712 449.9.

* cited by examiner

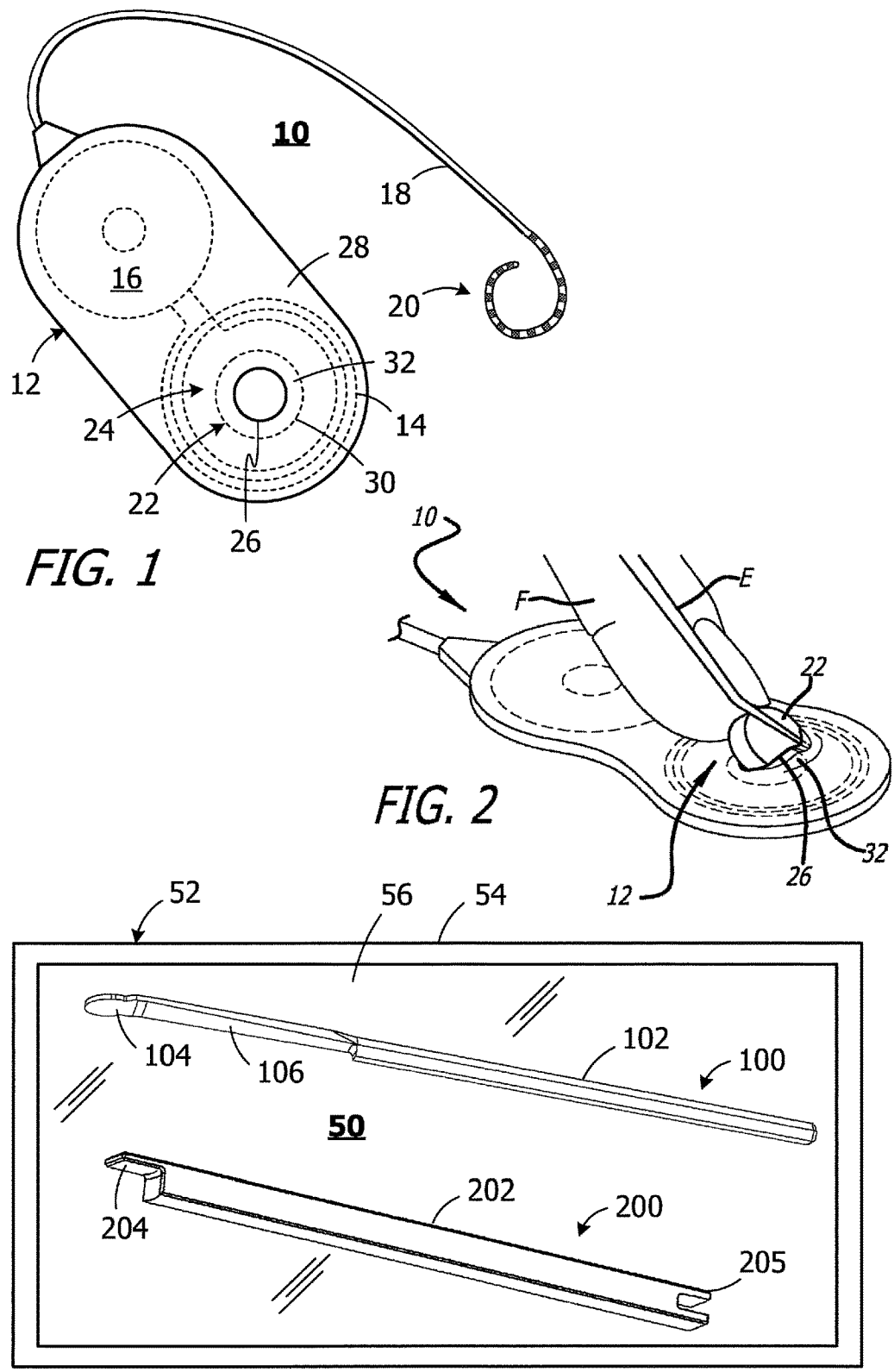

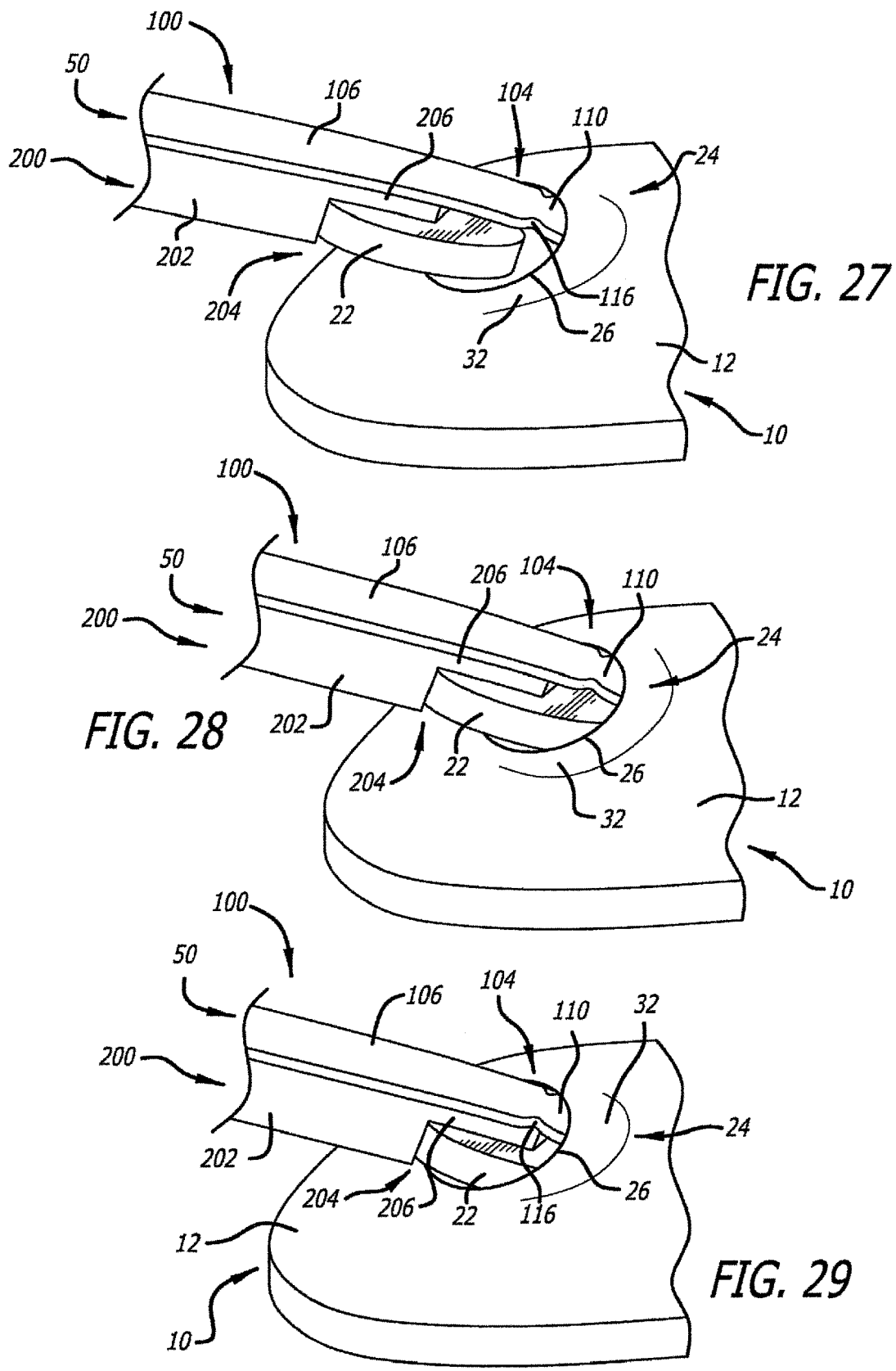

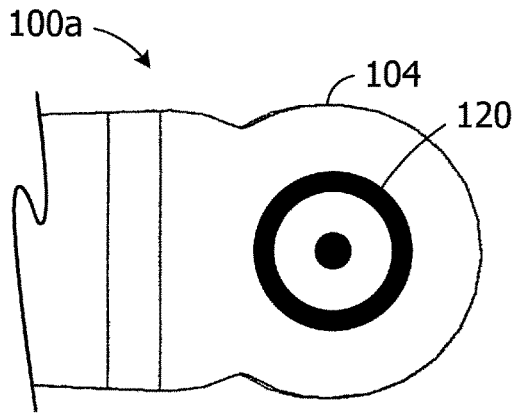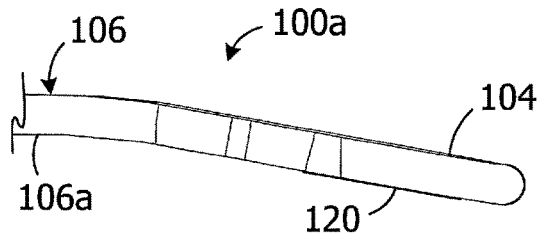
*FIG. 33*  *FIG. 34*
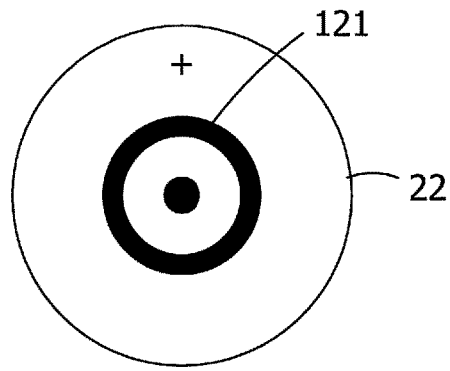
*FIG. 35*
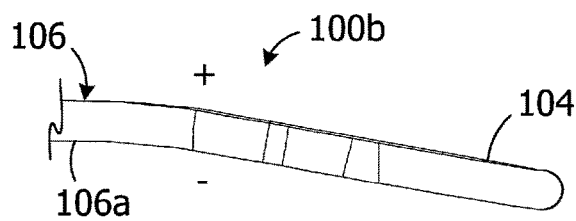
*FIG. 36*

MAGNET INSTALLATION SYSTEMS AND METHODS FOR USE WITH COCHLEAR IMPLANTS

CROSS-REFERENCE TO RELATED APPLICATIONS

This application is a divisional of U.S. application Ser. No. 14/764,792, filed Jul. 30, 2015, now U.S. Pat. No. 10,124,167, which is the U.S. National Stage of PCT App. Ser. No. PCT/US2014/019970, filed Mar. 3, 2014, which claims priority to U.S. Prov. App. Ser. No. 61/780,977, filed Mar. 13, 2013.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Sound processor With Remote Control" and incorporated herein by reference in its entirety.

As alluded to above, some ICS systems include an implant, a sound processor unit (e.g., a body worn processor or behind-the-ear processor), and a microphone that is in communication with the sound processor unit. The implant communicates with the sound processor unit and, to that end, some ICS systems include a headpiece, with a microphone, that is in communication with both the sound processor unit and the implantable device. The headpiece communicates with the implantable device by way of a transmitter (e.g., an antenna) on the headpiece and a receiver (e.g., an antenna) on the implant. Optimum communication is achieved when the transmitter and the receiver are aligned with one another. To that end, the headpiece and the implant include respective positioning magnets that are attracted to one another, and that maintain the position of the headpiece transmitter over the implant receiver.

One issue associated with ICS systems is that it is sometimes necessary to remove the magnet from the cochlear implant and then reinsert the magnet into the cochlear implant. Removal and reinstallation of the magnet preferably occurs in situ, i.e., with the cochlear implant secured to bone and accessed by way of an incision in the skin. For example, magnets are not compatible magnetic resonance imaging ("MRI") systems. Surgical procedures may be performed before and after the MRI procedure to remove and then replace the implant magnet, thereby obviating the need to remove and replace the entire implant. To that end, the implant includes a pocket formed from a resilient material (e.g., silicone) and an opening that is configured to stretch and permit surgical removal and replacement of the implant magnet.

The present inventors have determined that conventional instruments for removing and replacing the implant magnet are susceptible to improvement. For example, the present inventors have determined that it would be desirable to provide instruments that, as compared to conventional instruments, facilitate smaller surgical incision sizes and decrease the likelihood that the resilient pocket will be damaged during magnet removal and installation.

SUMMARY

A cochlear implant magnet installation system for use with a cochlear implant that includes a resilient housing, a magnet pocket, a magnet aperture having an aperture diameter, and a magnet having a magnet diameter that is greater than the aperture diameter. The installation system includes an installation device, including a handle portion and a distal portion, to which the magnet may be magnetically secured, and a guide including a handle portion and a first end portion that is configured to separate a magnet that is magnetically secured to the distal portion from the distal portion.

A cochlear implant magnet installation device for use with a cochlear implant that includes a resilient housing, a magnet pocket, a magnet aperture having an aperture diameter, and a magnet having a magnet diameter that is greater than the aperture diameter. The installation device includes a handle portion and a distal portion operably connected to the handle portion, the distal portion including a curved tip defining a tip width that is greater than the aperture diameter.

A method of installing a magnet having a magnet diameter into a cochlear implant that includes a resilient housing, a magnet pocket, a magnet aperture having an aperture diameter that is less than the magnet diameter. The method includes the steps inserting an installation device, which is carrying the magnet, into the magnet aperture such that a portion of the installation device that is wider than the magnet aperture stretches the magnet aperture, and moving the magnet off the installation device and into the magnet pocket.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a plan view of a conventional cochlear implant.

FIG. 2 is a perspective view of a conventional magnet installation method.

FIG. 3 is a plan view of a magnet installation system in accordance with one embodiment of a present invention.

FIG. 27 is a perspective view of another portion of the magnet installation method.

FIG. 28 is a perspective view of another portion of the magnet installation method.

FIG. 29 is a perspective view of another portion of the magnet installation method.

FIG. 33 is a bottom view of the distal portion of a magnet installation instrument in accordance with one embodiment of a present invention.

FIG. 34 is a side view of the distal portion of the magnet installation instrument illustrated in FIG. 33.

FIG. 35 is a top view of a magnet in accordance with one embodiment of a present invention.

FIG. 36 is a side view of the distal portion of a magnet installation instrument in accordance with one embodiment of a present invention.

DETAILED DESCRIPTION OF THE EXEMPLARY EMBODIMENTS

Figure 4:
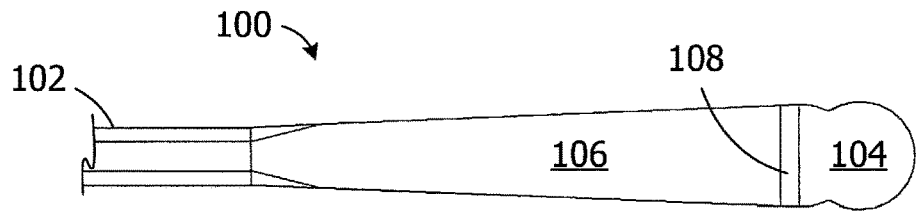
FIG. 4 is a top view of a portion of a magnet installation instrument in accordance with one embodiment of a present invention.

The following is a detailed description of the best presently known modes of carrying out the inventions. This description is not to be taken in a limiting sense, but is made merely for the purpose of illustrating the general principles of the inventions.

One example of a cochlear implant is generally represented by reference numeral 10 in FIG. 1. Cochlear implant 10 includes a flexible housing 12 formed from a silicone elastomer or other suitable material, an antenna 14, an internal processor 16, a cochlear lead 18 with an electrode array 20, and a positioning magnet 22 that is carried within an internal magnet pocket 24. The magnet 22 may be inserted into housing 12, and removed from the housing, by way of a magnet aperture 26 that extends through the top wall 28 of the housing. The magnet 22 is larger than the magnet aperture 26, i.e., the outer diameter of the magnet is greater than the diameter of the magnet aperture. In the illustrated embodiment, the diameter of the magnet is about 10.5 mm and the diameter of the magnet aperture is about 6 mm. The portion of the top wall 28 between the aperture 26 and the outer edge 30 of the magnet 22 forms a retainer 32 that, absent deformation of the aperture and retainer, prevents the magnet from coming out of the housing 12. The width of the retainer 32 is about 2.3 mm. During installation and removal, the aperture 26 and retainer 32 must be stretched or otherwise deformed so that the magnet 22 can pass through an aperture (i.e., aperture 26) that is smaller than the magnet when it is in its unstressed state.

As is described in greater detail below, the present systems allow magnet removal and installation procedures to be performed in a manner that is less likely (as compared to conventional apparatus and methods) to damage the magnet aperture 26 or other portions of the elastomeric housing 12, thereby requiring explanation of the entire cochlear implant 10. To that end, one example of a conventional magnet insertion procedure is illustrated in FIG. 2. After the magnet 22 has been positioned adjacent to the aperture 26, the surgeon uses a finger F to press the magnet through the smaller aperture while a conventional elevator E, or other surgical instrument, is used to deflect the retainer 32. The elevator E is then pivoted away from the implant 10 and the elevator tip is pushed around the perimeter of the aperture 26 to force the remainder of the magnet 22 under the retainer 32. The present inventors have determined that the conventional method and instrument require a larger than optimal incision and may result in damage to the elastomeric housing 12 at or near the aperture 26 and retainer 32. For example, the use of a finger F and pivoting of the elevator E requires relatively large incision. The narrow tip of the elevator E results in a significant amount of force being applied to a small area on the retainer 32, which creates a region of concentrated retainer stress that may result in damage to the retainer.

As illustrated in FIG. 3, one example of a magnet installation system (or "kit") 50 in accordance with at least one of the present inventions includes a magnet installation instrument ("installation instrument") 100 and a magnet guide ("guide") 200. The installation instrument 100 includes a proximal handle portion 102, a distal portion 104 and a tapered portion 106, while the guide 200 includes a handle portion 202, a first end portion 204 and a second end portion 205. The installation instrument 100 and guide 200 are stored in packaging 52, which in the illustrated implementation includes a box or other enclosure 54 with a cover 56. The cover may be transparent as shown.

Figure 5:
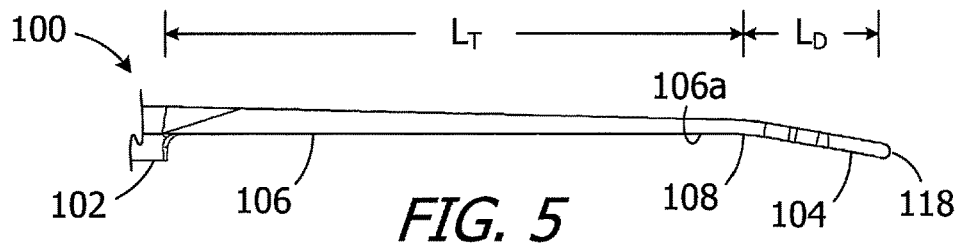
FIG. 5 is side view of the magnet installation instrument illustrated in FIG. 4.
Figure 6:
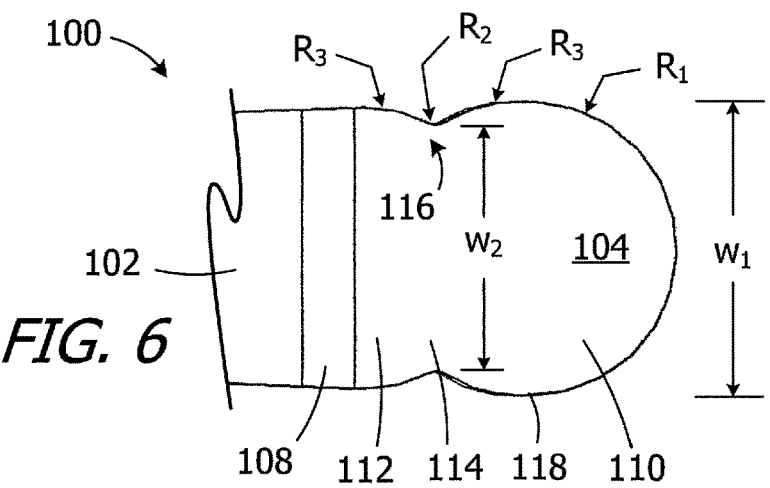
FIG. 6 is an enlarged top view of the distal portion of the magnet installation instrument illustrated in FIG. 4.
Figure 7:
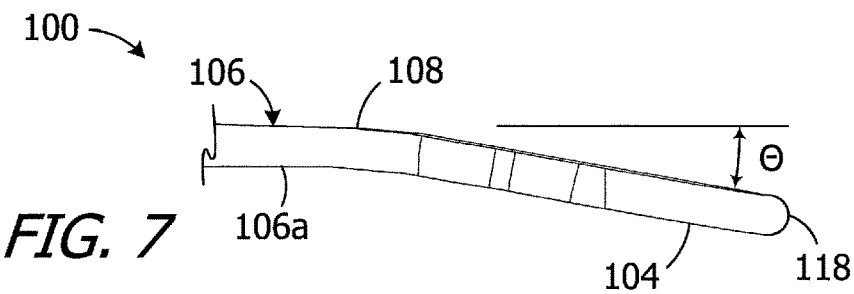
FIG. 7 is an enlarged side view of the distal portion of the magnet installation instrument illustrated in FIG. 4.
Figure 8:
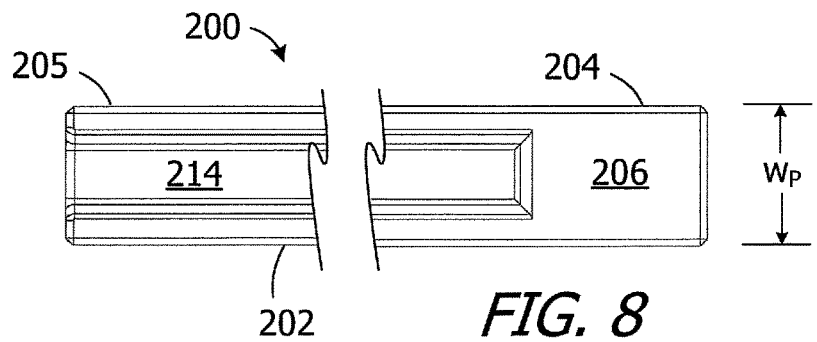
FIG. 8 is a top view of a magnet guide in accordance with one embodiment of a present invention.
Figure 9:
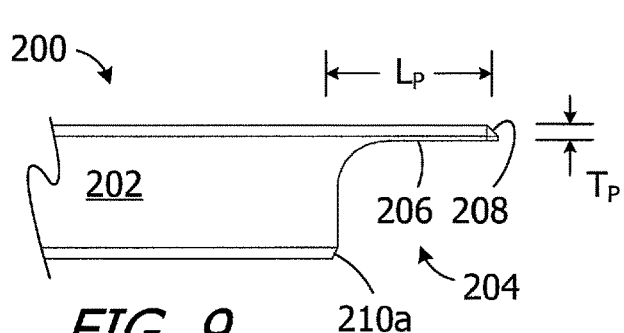
FIG. 9 is a side view of a first end portion of the magnet guide illustrated in FIG. 8.
Figure 10:
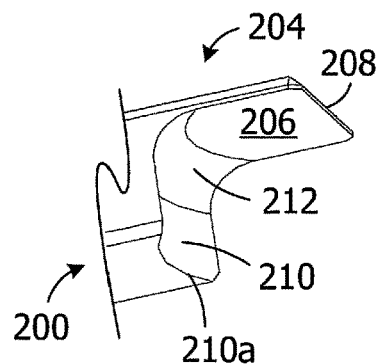
FIG. 10 is a perspective view the first end portion of the magnet guide illustrated in FIG. 8.
Figure 11:
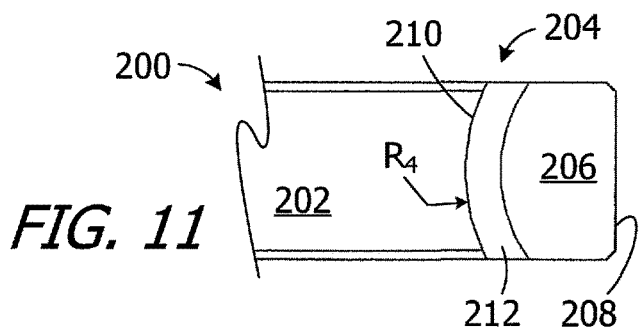
FIG. 11 is a bottom view of the first end portion of the magnet guide illustrated in FIG. 8.

The exemplary installation instrument 100 is configured such that it may be inserted with the guide 200 through a relatively small incision (i.e., an incision that is about 10 to 25 mm in length as determined by the thickness of tissue over the implant site) and access, for example, the magnet 22 under the retainer 32, without damaging the retainer or other portion of the associated housing. To that end, and referring to FIGS. 4-7, the installation instrument 100 includes, as noted above, a proximal handle portion 102, a distal portion 104 and an intermediate portion, such as the exemplary tapered portion 106, which connects the handle portion to the distal portion. The distal portion 104 and tapered portion 106, which are thinner than the handle portion 102, are separated by a bent portion 108 such that an angle Θ is defined by the distal and tapered portions. The angle Θ is relatively small and the bent portion 108 augments usability by providing a better line of sight for the surgeon. The distal portion 104 includes a curved tip 110 and a base 112 with a narrowed region 114 therebetween. The narrowed region 114 is defined by a pair of indentations 116 that are located proximal of the tip 110. The narrowed region 114 provides a region that reduces the stress on the retainer 32 after the tip 110 has been fully inserted through the aperture 26 and into the magnet pocket 24, as is discussed in greater detail below. The distal portion 104, or the distal and tapered portions 104 and 106, may be provided with a curved or otherwise non-sharp edge 118 (note FIGS. 5 and 7). The tapered portion 106 includes a magnet support surface 106a where the magnet 22 is initially positioned during the installation process, as is discussed below with reference to FIG. 26. Suitable materials for the installation instrument include magnetic metals such as magnetic steel.

The dimensions of the distal portion 104 may in some instances, including the illustrated implementation, depend upon the configuration and dimensions of certain aspects of the associated cochlear implant. With respect to the exemplary cochlear implant 10, and as noted above, the diameter of the magnet 22 is about 10.5 mm, the diameter of the magnet aperture 26 is about 6 mm, and the width of the deflectable retainer 32, i.e., the distance between the aperture edge and the magnet outer edge 30, is about 2.3 mm. Turning to the exemplary installation instrument 100, the length $L_D$ of the distal portion 104 is about 10.8 mm, the length $L_T$ of the tapered portion 106 is about 39.2 mm and the angle Θ is about 10°. The maximum width of the distal portion tip 110 is about 70 to 95% of the diameter of the magnet 22, and is about 130 to 165% of the diameter of the magnet aperture 26. As a result, when it is inserted through the magnet aperture 26, the distal portion tip 110 will stretch the aperture 26 and deform the retainer 32. However, in contrast to the elevator that is used in conventional magnet insertion procedures, the distal portion tip 110 will apply force over a much greater area, thereby reducing the likelihood that there will be stress concentrations which are significant enough to result in damage to the retainer 32. In the illustrated implementation, the width $W_1$ of the distal portion tip 110, which is the maximum width, is about 8.5 mm, while the width $W_2$ of the narrowed region 114 is about 6.6 mm. The widths $W_1$ and $W_2$ are perpendicular to the longitudinal axis of the handle 102. The exemplary distal portion tip 110 is substantially circular and, accordingly, the radius $R_1$ is ½$W_1$ (i.e., about 4.3 mm). In other implementations, the distal portion tip 110 may be non-circular, e.g., somewhat elliptical. Radius $R_2$ is about 0.5 mm, while radii $R_3$ are about 2.3 mm. Radii $R_2$ and $R_3$ provide smooth transitions at and around the indentations 116. The handle portion 102 (FIG. 3) may be any suitable length and, in the illustrated example, is about 100 mm. It should also be noted that, as used herein, the term "about" means ±10%.

The exemplary magnet guide 200 illustrated in FIGS. 8-13 includes a handle portion 202 and end portions 204 and 205. The first end portion 204 is configured to separate the magnet 22 from the installation instrument 100 during the installation process. The second end portion 205 may be used, in some procedures, to insert a non-magnetic plug (e.g., a titanium plug) into the cochlear implant magnet pocket 24 after the magnet 22 has been removed.

The non-magnetic plug occupies the volume normally occupied by magnet while the magnet is removed to prevent ingress of body tissue into the magnet pocket 24. Suitable materials for the guide 200 include autoclavable plastics such as Polypropylene (PP), Polycarbonate (PC), Polymethylpentene (PMP), PTFE Resin, Liquid Crystal Polymer (LCP), Fluorinated ethylene propylene (FEP), Ethylene tetrafluoroethylene (ETFE), Polychlorotrifluoroethylene (PCTFE), Polyethylene terephthalate (PET), Polyoxymethylene (POM) and Polyamide (PA), and non-magnetic metals such as non-magnetic stainless steel.

The first end portion 204 illustrated in FIGS. 8-11 has a thin projection 206 with a beveled edge 208. The thin projection 206 is positioned between portions of the magnet 22 and the magnet support surface 106a during the installation process. The first end portion 204 also has an inwardly curved abutment 210, with a bottom corner 210a, and a transition surface 212. In the illustrated implementation, the projection 206 has a width $W_P$ of about 5 mm, a length $L_P$ of about 6.3 mm, and a thickness $T_P$ of about 1 mm. The curvature of the abutment 210 may approximate that of the magnet 22 and, accordingly, $R_4$ (FIG. 11) is about 5.3 mm. The transition surface 212 conforms to the curved shape of the magnet edges. It should also be noted that the top surface of the magnet guide 200 includes a longitudinally extending groove 214 that extends from a point adjacent to the thin projection 206 to and through the second end portion 205. The respective sizes and shapes of the handle portion 102 and the groove 214 are such that the handle portion and groove register with one another. As such, the installation instrument 100 and magnet guide 200 will remain aligned with one another, with their longitudinal axes parallel. The handle portion 102 and groove 214 may also be used to direct the guide 200 along the installation instrument 100 as the guide pushes the magnet during the installation described below with reference to FIGS. 19-25.

Figure 12:
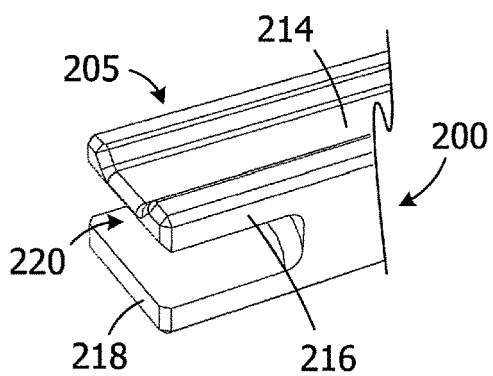
FIG. 12 is a perspective view of a second end portion of the magnet guide illustrated in FIG. 8.
Figure 13:
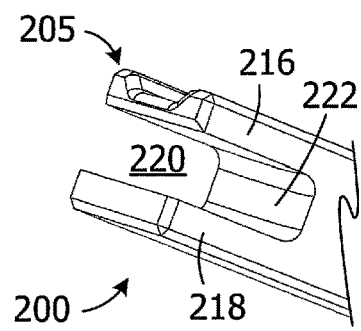
FIG. 13 is another perspective view of the second end portion of the magnet guide illustrated in FIG. 8.
Figure 14:
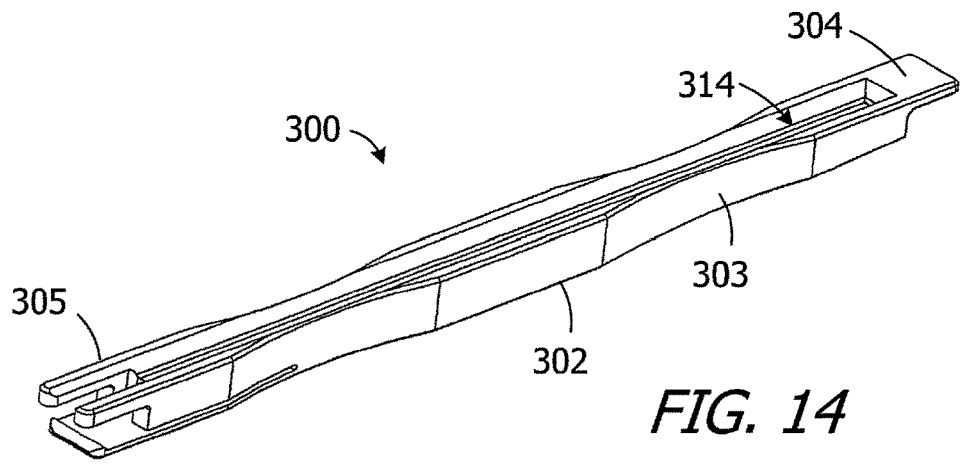
FIG. 14 is a perspective view of a magnet guide in accordance with one embodiment of a present invention.
Figure 15:
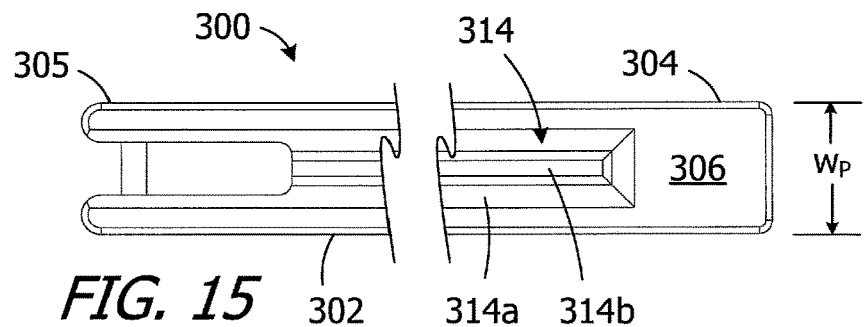
FIG. 15 is a top view of the magnet guide illustrated in FIG. 14.

Referring to FIGS. 12 and 13, the second end portion 205 of the exemplary guide 200 includes a pair of projections 216 and 218 that are separated by a gap 220 and together form a connector that holds a non-magnetic plug. The non-magnetic plug will rest within the gap 220 against a curved surface 222. In at least some instances, the distance between the projections 216 and 218 will be slightly less than the thickness of the plug so that the plug will be held by the connector. The force with which the plug is held should be low so that the plug will slide out of the connector, when engaged by the retainer 32, as the guide is pulled proximally after the plug is positioned in the magnet pocket 24.

Another exemplary magnet guide, which is generally represented by reference numeral 300 in FIGS. 14-20, includes a handle portion 302 with thumb rests 303 and also includes end portions 304 and 305. The first end portion 304 is configured to separate the magnet 22 from the installation instrument 100 during the installation process. The second end portion 305 may be used, in some procedures, to insert a non-magnetic plug into the cochlear implant magnet pocket 24 after the magnet 22 has been removed and, as discussed below, the second end portion is configured to have a cooperative relationship with an elevator or similar surgical instrument. The exemplary magnet guide 300 may be formed from the same materials as the magnet guide 200, and may be provided in the magnet installation system 50 illustrated in FIG. 3 in place of the magnet guide 200.

Figure 16:
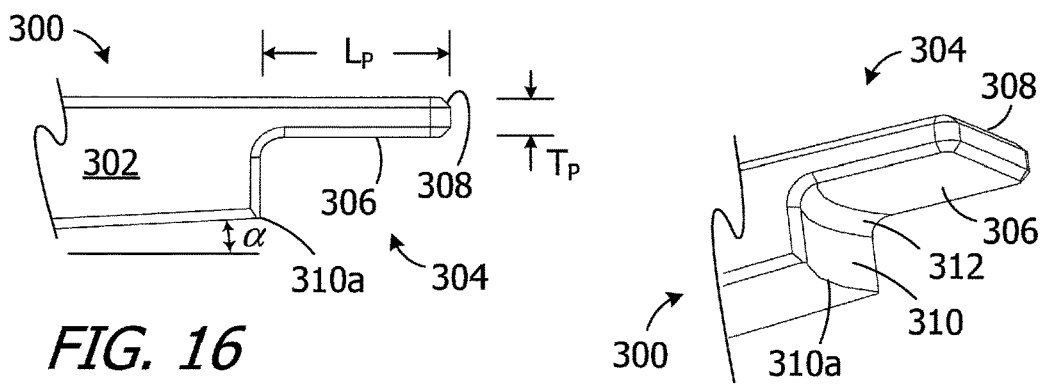
FIG. 16 is a side view of a first end portion of the magnet guide illustrated in FIG. 14.
Figure 17:
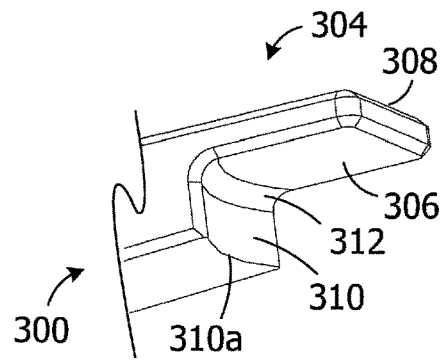
FIG. 17 is a perspective view the first end portion of the magnet guide illustrated in FIG. 14.
Figure 18:
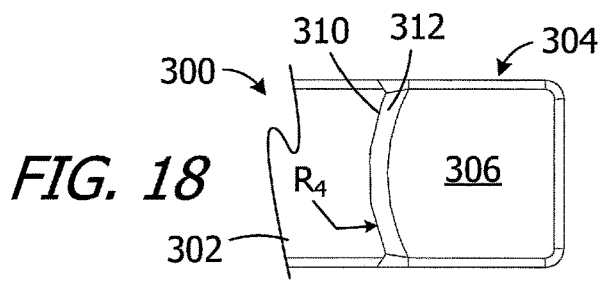
FIG. 18 is a bottom view of the first end portion of the magnet guide illustrated in FIG. 14.

Referring to FIGS. 16-18, the first end portion 304 has a thin projection 306 (with beveled edges 308) that is positioned between portions of the magnet 22 and the magnet support surface 106a during the installation process, an inwardly curved abutment 310 (with a bottom corner 310a) and a transition surface 312. In the illustrated implementation, the projection 306 has a width $W_P$ of about 5.0 mm, a length $L_P$ of about 5.3 mm, and a thickness $T_P$ of about 1.0 mm, while the abutment 310 has a radius of curvature $R_4$ (FIG. 18) of about 5.3 mm. The bottom surface of the handle portion 302 is angled in the region adjacent to the corner 310a, thereby reducing the thickness of the handle portion in that region. Angle α is about 3° in the illustrated implementation and may vary as appropriate. The reduced thickness makes it less likely that the movement of the guide 300 will be interfered with during insertion of the magnet 22 into the pocket 24.

The top surface of the magnet guide 300 includes a longitudinally extending groove 314, with sloped walls 314a and a clearance recess 314b, that extends from a point adjacent to the thin projection 306 to the gaps 324 and 328 (FIG. 20) in the second end portion 305. The respective sizes and shapes of the handle portion 102 and the groove 314 are such that the handle portion and groove register with one another and there is a small gap between the handle portion and the bottom of the clearance recess 314b. As such, the installation instrument 100 and magnet guide 300 will remain aligned with one another, with their longitudinal axes parallel. The handle portion 102 and groove 314 may also be used to direct the guide 300 along the installation instrument 100 as the guide pushes the magnet during the installation process described below with reference to FIGS. 26-32.

Figure 19:
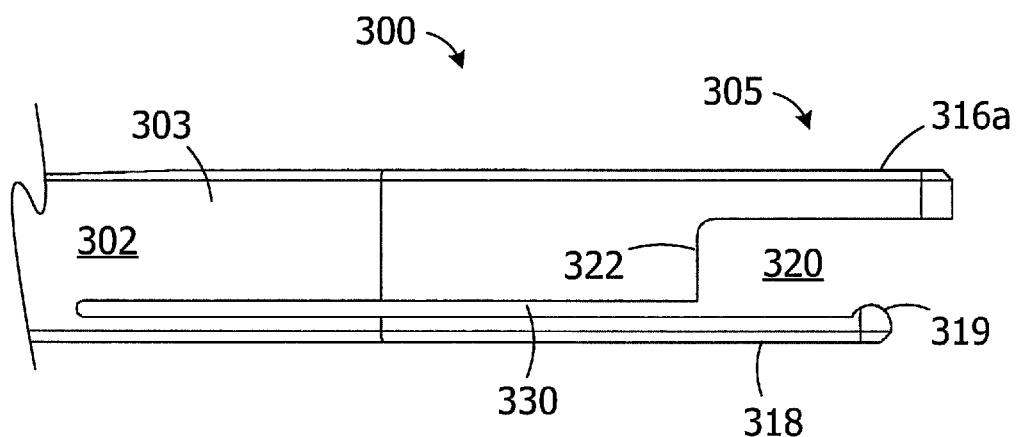
FIG. 19 is a side view of a second end portion of the magnet guide illustrated in FIG. 14.
Figure 20:
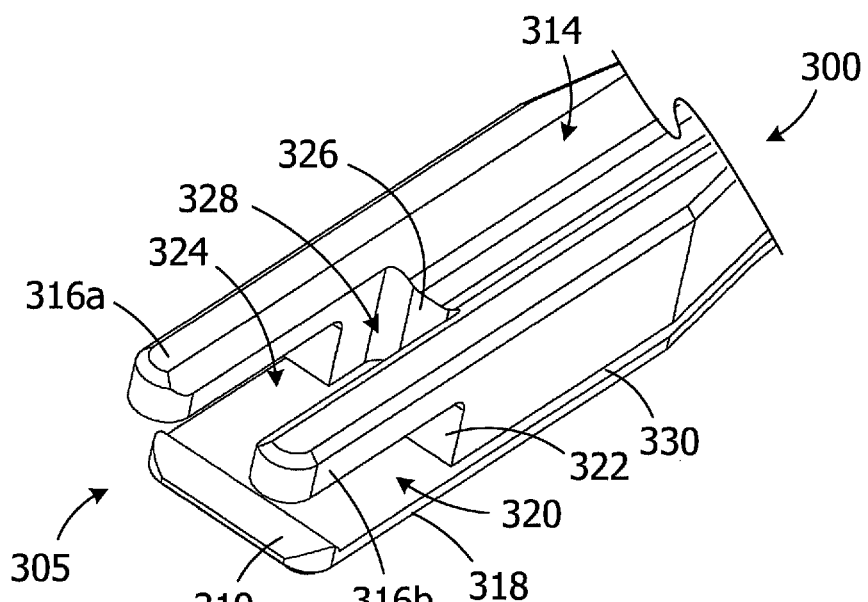
FIG. 20 is a perspective view of the second end portion of the magnet guide illustrated in FIG. 14.
Figure 21:
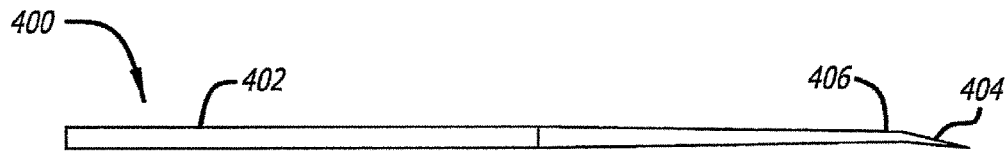
FIG. 21 is a side view of a conventional surgical instrument.

Referring to FIGS. 19 and 20, the second end portion 305 of the exemplary guide 200 includes a pair of first projections 316a and 316b and a second projection 318. The first projections 316a and 316b are separated from the second projection 318 by a gap 320 and together form a connector that holds a non-magnetic plug. The non-magnetic plug will rest within the gap 320 against surfaces 322, which may be flat or curved. The free end of the second projection 318 includes a cam 319. The plug slides over the cam 319 and into the gap 320. The relative dimensions of the plug and gap 320 may be such that the cam will engage the approximate center of the plug.

The first projections 316a and 316b are separated by a gap 324, while the walls 322 are separated from wall 326 by a gap 328. The distance between the first projections 316a and 316b and the cam 319 may be slightly less than the thickness of the plug so that the plug will be held by the connector. To accommodate plugs that may be slightly larger than expected, a portion of the projection 318 that would otherwise be integral with the handle portion 302 is separated from the handle portion by a slot 330. The slot 330 allows the projection 318 to move a greater distance from first projections 316a and 316b than it otherwise would. The gaps 324 and 328 allow a surgical instrument, such as the elevator 400 (discussed below), to engage the plug and push the plug out of the gap 320 and into the magnet pocket 24.

As alluded to above, the installation instrument 100 and a guide 200 (or the guide 300) may be used in conjunction with an elevator, such as the House "Gimmick" elevator, or similar surgical instrument. One example of such an instrument is generally identified by reference numeral 400 in FIG. 21. The elevator or similar surgical instrument may be separately provided. In some implementations, the magnet installation system may itself include the elevator or similar surgical instrument. Typically, the elevator would be employed in those instances where the surgeon does not properly complete the magnet removal and/or insertion processes described below with reference to FIGS. 22-32. The elevator may also be used to push a non-magnetic plug out of the guide 300. The exemplary elevator 400 illustrated in FIG. 21 includes a handle 402, a tip 404 and a bent portion 406. The tip 404 is about 12 mm in length and about 1 mm in width and the bend is about 15°.

Referring to FIGS. 22-25, the exemplary installation instrument 100 may be used in a magnet removal method. The method is performed in situ, i.e., with the cochlear implant 10 positioned under the skin, and a small incision is made to gain access to the implant housing 12. The incision is linear and is about 10 mm to 25 mm in length, as compared to the incisions of about 50 mm associated with conventional methods and apparatus. Nevertheless, for explanatory purposes, only the cochlear implant 10 and installation instrument 100 are shown in FIG. 22-25. The cochlear implant 10, as is discussed in greater detail above, includes an elastomeric housing 12 and a magnet 22 located within an internal magnet pocket 24. The magnet 22, which can be inserted and removed by way of the magnet aperture 26, is held in place with the retainer 32.

Figure 22:
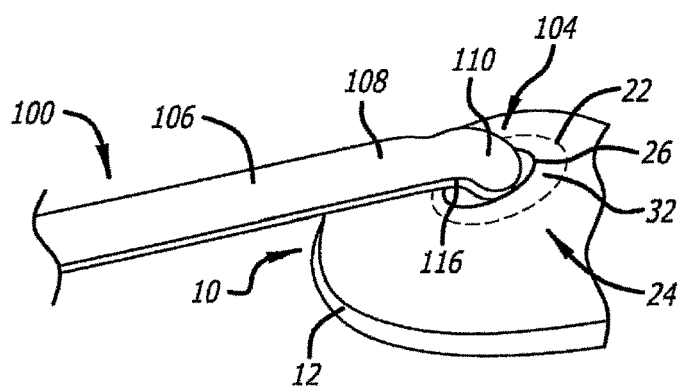
FIG. 22 is a perspective view of a portion of a magnet removal method in accordance with one embodiment of a present invention.
Figure 23:
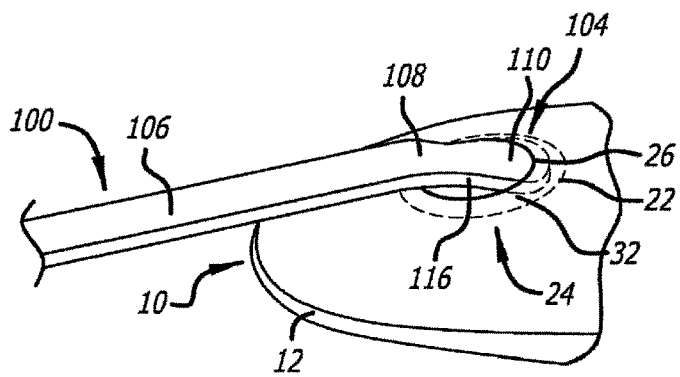
FIG. 23 is a perspective view of another portion of the magnet removal method.
Figure 24:
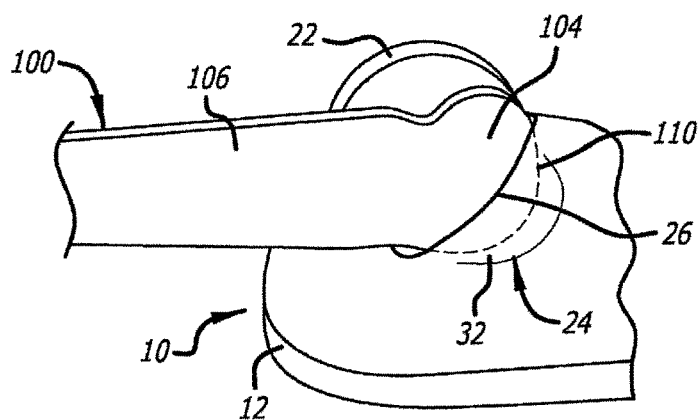
FIG. 24 is a perspective view of another portion of the magnet removal method.
Figure 25:
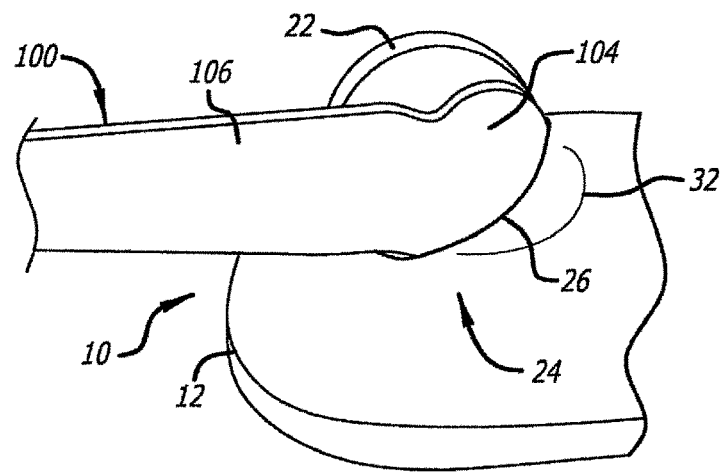
FIG. 25 is a perspective view of another portion of the magnet removal method.

After access to the cochlear implant 10 has been obtained by way of the incision, the installation instrument 100 is positioned relative to the cochlear implant such that the distal portion 104 is adjacent to the magnet aperture 26 (FIG. 22). The distal portion tip 110 may then be moved through the aperture 26 and under the retainer 32 (FIG. 23). The aperture 26 will continue to be stretched by the tip 110 as the installation instrument 100 moves distally until the narrowed region 114, and indentations 116, reach the aperture. The magnetic attraction between the magnet 22 and the magnetic material from which the installation instrument 100 is formed will cause the magnet to adhere to the distal portion 104. The surgeon may then remove the magnet 22 from the pocket 24. In the illustrated example, the installation instrument 100 is rotated about its longitudinal axis (FIG. 24) so that one side of the distal portion 104 and the attached magnet 22 will pop through the aperture 26 and past the retainer 32. The aperture 26 and retainer 32 will begin to return to their unstressed state. As the installation instrument 100 continues to rotate about its longitudinal axis (FIG. 25), the remainders of the distal portion 104 and the attached magnet 22 will pass through the aperture 26. The magnet 22 is now completely out of the pocket 24, and the aperture 26 and retainer 32 have returned to their unstressed state. The installation instrument 100 (and attached magnet 22) may then be removed from the patient.

It should be noted here that the insertion instrument 100 remains substantially parallel to the implant 100 during the magnet removal process, which facilitates the use of a small incision.

Turning to FIGS. 26-32, the installation instrument 100 and guide 200 of the exemplary system 50 may be used in the magnet installation method illustrated therein. Here too, although method is performed in situ, only the cochlear implant 10, the installation instrument 100 and the guide 200 are shown for explanatory purposes. Of course, the method may also be performed outside the body when a magnet is initially placed into the housing 12 as part of the implant assembly process.

Figure 26:
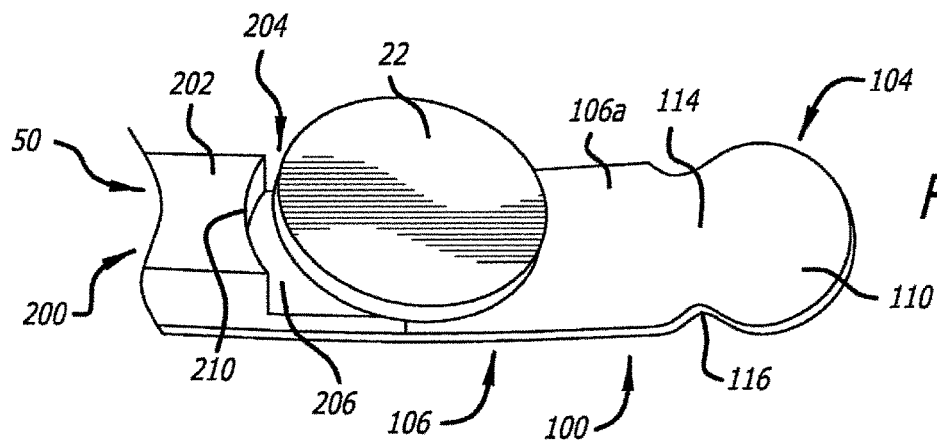
FIG. 26 is a bottom view showing a magnet carried by a magnet installation system in accordance with one embodiment of a present invention.

At the outset, the installation instrument 100 and the guide 200 of the installation system 50 may be placed against one another in the manner illustrated in FIG. 26. Here, the top surface of the magnet guide 200 abuts the bottom surface of the installation instrument 100, with the handle portion 102 located within the groove 214 (note FIGS. 3 and 8). The thin projection 206 of the guide 200 is aligned with the tapered portion magnet support surface 106a. The magnet 22 will then be positioned on the first end portion 204 of the guide 200, with the proximal end of the magnet located near or against the abutment 210 and the transition surface 212 (FIGS. 10 and 11) and the thin projection 206 located between a portion of the magnet and the magnet support surface 106a. The magnetic attraction between the magnet and the installation instrument 100 will secure the magnet to the system 50 despite the presence of the non-magnetic guide projection 206. In other words, the length, width and thickness of the non-magnetic guide projection 206 are together insufficient to prevent the magnet 22 from being initially secured to the installation instrument 100. Additionally, the guide projection 206 maintains the spatial relationship between the guide 200 and the magnet 22, i.e. the proper alignment, which is necessary for the guide to facilitate removal of the magnet from the installation instrument 100 in the manner described below.

Figure 26A:
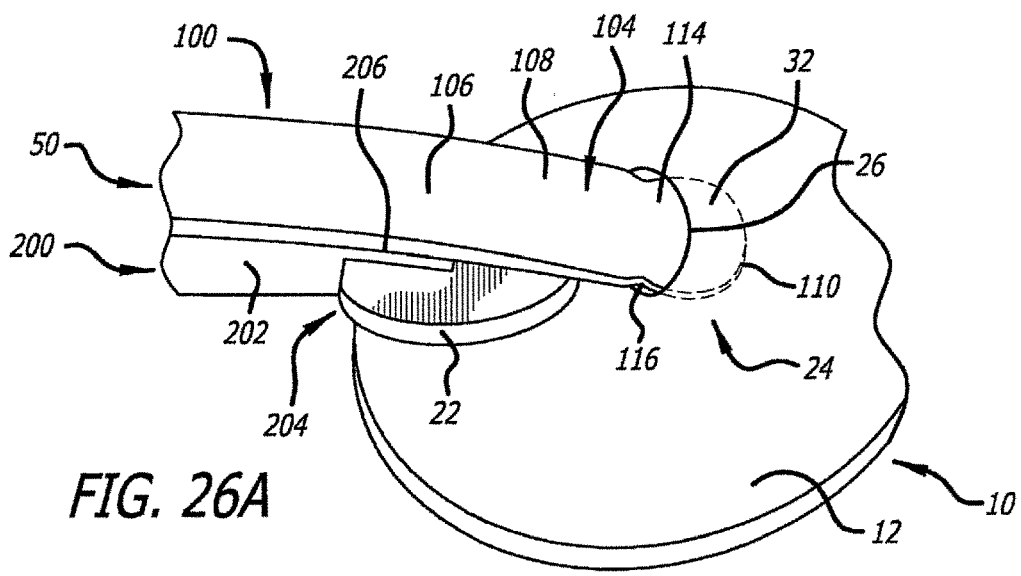
FIG. 26A is a perspective view of a portion of a magnet installation method in accordance with one embodiment of a present invention.
Figure 30:
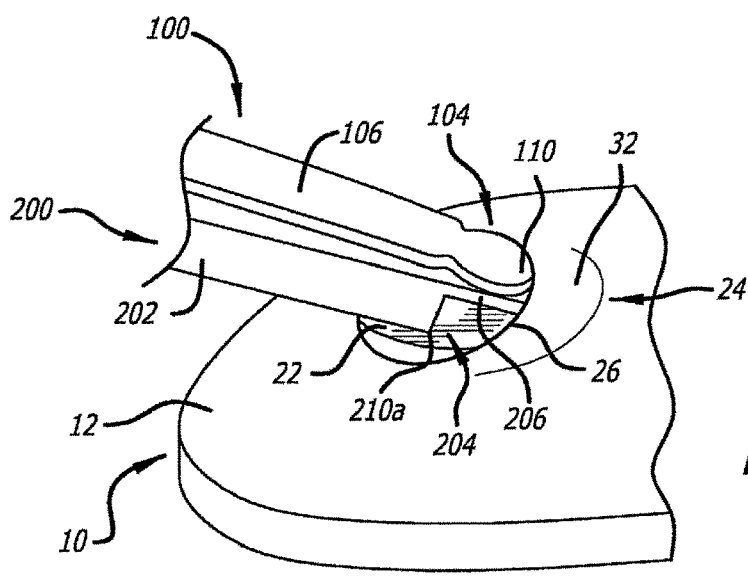
FIG. 30 is a perspective view of another portion of the magnet installation method.
Figure 31:
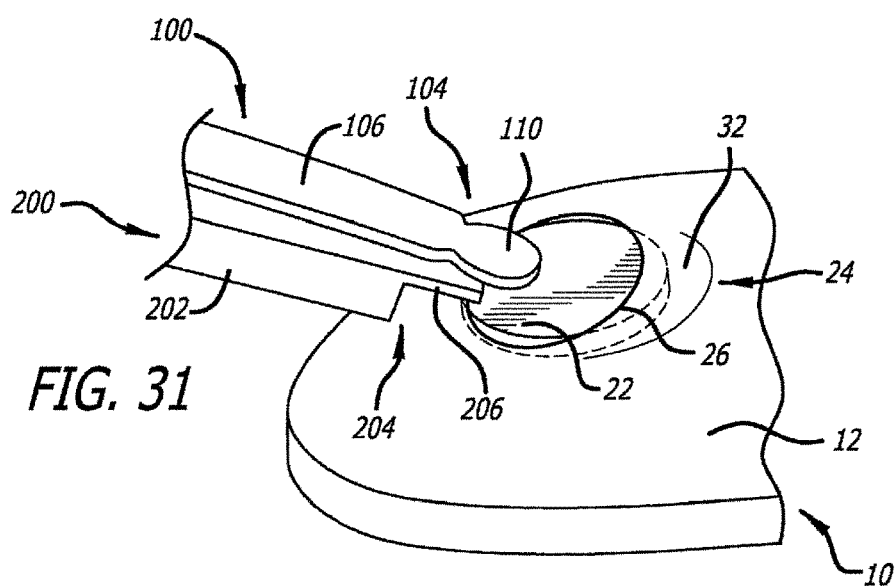
FIG. 31 is a perspective view of another portion of the magnet installation method.
Figure 32:
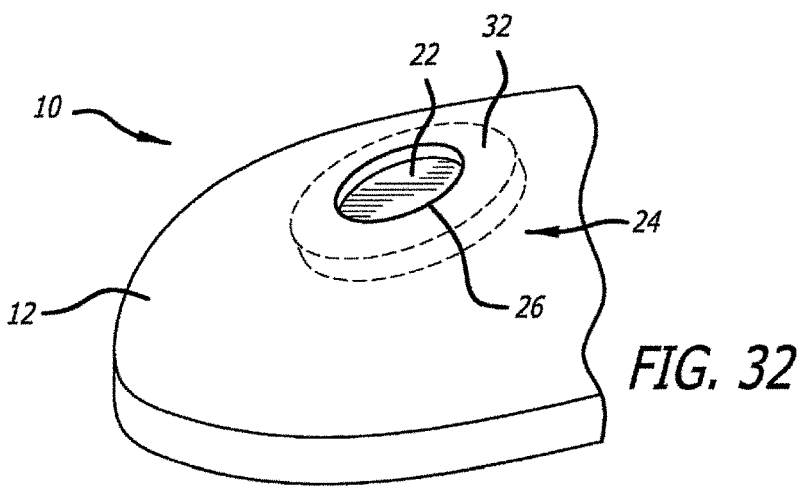
FIG. 32 is a perspective view of another portion of the magnet installation method.

After access to the magnet-less implant 10 has been obtained by way of an incision, the installation system 50 and magnet 22 may be moved to a position adjacent the cochlear implant 10. Next, as illustrated in FIG. 26A, the system 50 may be inserted into the cochlear implant 10 such that the distal tip 110 of the installation instrument distal portion 104 enters the empty magnet pocket 24, by way of the aperture 26, and slides under the retainer 32. The aperture 26 will be stretched by the tip 110 until the narrowed region 114, and the indentations 116, reach the aperture. The magnet 22 remains outside the aperture 26. The guide 200 may then be used to move the magnet 22 a short distance distally relative to the installation instrument 100 (FIG. 27) so that the magnet is partially within the aperture 26, and the installation system 50 may be pivoted slightly relative to the implant 10. The installation instrument distal portion 110 will continue to deform the aperture 26 and retainer 32 as the installation system 50 pivots. With the installation instrument 100 held in place, distal movement of the guide 200 may be used to push the magnet 22 through the aperture 26 and about 50% into the pocket 24 (FIGS. 28 and 29). Continued distal movement of the guide 200 will separate the magnet 22 from the installation instrument 100 and, eventually, the abutment bottom corner 210a will slide up and over the top surface of the magnet 22 (FIG. 30). The installation instrument 100, and then the guide 200, may be pulled proximally out from under the retainer 32 and through the magnet aperture 26 (FIG. 31). If necessary, the installation instrument tip 110 may be used to press any portion of the magnet 22 that is within the aperture 26 but not already under retainer 32 down into the pocket 24. This will allow the remainder of the aperture 26 to pass over the magnet 22 and return to its unstressed state (FIG. 32), with the magnet 22 in the pocket 24 and under the retainer 32, thereby completing the installation.

The method described above with reference to FIGS. 26-32 may also be performed with the guide 300 in place of the guide 200.

It should also be noted here that, during the magnet installation method performed with the system 50, the angle between the system and the implant 10 is relatively small, thereby facilitating the use of a relatively small incision.

The present inventors have determined that another aspect of magnet installation is proper polar orientation, because an improperly oriented magnet will repel the corresponding magnet in the headpiece, and that it would be desirable for some aspect of the installation system to facilitate proper polar orientation. One example of an installation instrument that is configured to facilitate proper polar orientation of the magnet is generally represented by reference numeral 100a in FIGS. 33 and 34. Installation instrument 100a is essentially identical to installation instrument 100 and similar elements are represented by similar reference numerals. Here, however, the bottom surface of the distal portion 104 and/or tapered portion 106 includes indicia 120. Magnets used with the present installation system may be provided with the same indicia (or other representative indicia) on the side of magnet with the polarity that is intended to face outwardly toward the cochlear implant headpiece. For example, the magnet 22a illustrated in FIG. 35 includes indicia 121 on the magnetic north ("+") side. The surgeon or surgical assistant can insure proper orientation of the magnet 22a by initially positioning the magnet 22a on the installation instrument 100a with the indicia 121 facing the side of the installation instrument with the indicia 120. The indicia may be formed by laser marking or other suitable processes. One or more magnets 22a including indicia, such as indicia 121, may be provided in a magnet installation magnet installation system (or "kit"), such as the system 50 illustrated in FIG. 3.

Alternatively, or in addition, the installation instrument may be polarized in such a manner that the magnet will only stick to the installation instrument in the proper orientation. The installation instrument 100b illustrated in FIG. 36, which is otherwise identical to installation instrument 100, is polarized such that the magnetic south ("−") side of the instrument is the same side as the magnet support surface 106a.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A method of installing a magnet having a magnet diameter into a cochlear implant, the cochlear implant including a resilient housing, a magnet pocket, a magnet aperture having an aperture diameter that is less than the magnet diameter, the method comprising:
   inserting an installation device, which is carrying the magnet, into the magnet aperture such that a portion of the installation device that is wider than the magnet aperture stretches the magnet aperture; and
   moving the magnet off the installation device and into the magnet pocket.

2. A method as claimed in claim 1, wherein
   moving the magnet comprises moving the magnet off the installation device and into the magnet pocket with a magnet guide.

3. A method as claimed in claim 2, further comprising;
   positioning the magnet guide against the installation device; and
   positioning the magnet on the installation device such that a portion of the magnet guide is located between the magnet and the installation device.

4. A method as claimed in claim 2, wherein
moving the magnet comprises moving at least one of the installation device and the magnet guide longitudinally relative to the other of the installation device and the magnet guide until the magnet slides off the installation device and into the magnet pocket.

5. A method as claimed in claim 1, wherein the magnet includes a side with magnet indicia and the installation device includes a side with installation device indicia, the method further comprising:
positioning the magnet on the installation device with the magnet side with magnet indicia faces the installation device side with installation device indicia.

6. A method, comprising:
inserting a portion of an installation device through a magnet aperture and into a magnet pocket of a resilient cochlear implant housing while a magnet is secured to the installation device; and
moving the magnet off the installation device and into the magnet pocket by moving at least one of the installation device and a magnet guide longitudinally relative to the other of the installation device and the magnet guide.

7. A method as claimed in claim 6, wherein
inserting the portion of the installation device through the magnet aperture comprises stretching the magnet aperture with the portion of the installation device as the portion of the installation device is inserted into the magnet aperture.

8. A method as claimed in claim 7, wherein
moving the magnet off the installation device and into the magnet pocket comprises moving the magnet off the installation device and into the magnet pocket while the magnet aperture is being stretched by the portion of the installation device.

9. A method as claimed in claim 6, further comprising:
positioning the magnet guide against the installation device; and
positioning the magnet on the installation device such that a portion of the magnet guide is located between the magnet and the installation device.

10. A method as claimed in claim 6, wherein
the magnet includes a side with magnet indicia and the installation device includes a side with installation device indicia; and
the magnet is secured to the installation device with the magnet side with magnet indicia facing the installation device side with installation device indicia.

11. A method as claimed in claim 6, wherein
the magnet guide is formed from non-magnetic material.

12. A method as claimed in claim 6, wherein
the installation device includes a handle;
the magnet guide includes a slot; and
the handle is within the slot when the at least one of the installation device and the magnet guide moves longitudinally relative to the other of the installation device and the magnet guide.

13. A method as claimed in claim 6, wherein
inserting the portion of the installation device through the magnet aperture and moving the magnet off the installation device and into the magnet pocket occur while the resilient cochlear implant housing is positioned under skin.

14. A method as claimed in claim 13, further comprising:
forming an incision in the skin prior to inserting the portion of the installation device through the magnet aperture and moving the magnet off the installation device and into the magnet pocket.

15. A method as claimed in claim 14, further comprising:
removing a magnet from the magnet pocket after the incision is formed and prior to inserting the portion of the installation device through the magnet aperture and moving the magnet off the installation device and into the magnet pocket.

16. A method as claimed in claim 14, further comprising;
removing a magnet from the magnet pocket with the installation device after the incision is formed and prior to inserting the portion of the installation device through the magnet aperture and moving the magnet off the installation device and into the magnet pocket.

\* \* \* \* \*